US010151696B2

(12) United States Patent
Yokoyama et al.

(10) Patent No.: US 10,151,696 B2
(45) Date of Patent: Dec. 11, 2018

(54) METHOD FOR DETERMINING ABNORMALITY IN PARTICLE ANALYZER AND PARTICLE ANALYZER

(71) Applicant: Sysmex Corporation, Kobe-shi, Hyogo (JP)

(72) Inventors: Koji Yokoyama, Kobe (JP); Hiromi Morisaki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 438 days.

(21) Appl. No.: 14/869,156

(22) Filed: Sep. 29, 2015

(65) Prior Publication Data

US 2016/0091428 A1   Mar. 31, 2016

(30) Foreign Application Priority Data

Sep. 30, 2014 (JP) .................. 2014-202184

(51) Int. Cl.
  *G01N 21/64* (2006.01)
  *G01N 15/14* (2006.01)
  *G01N 15/10* (2006.01)
  *G01N 35/00* (2006.01)

(52) U.S. Cl.
  CPC ..... *G01N 21/6428* (2013.01); *G01N 15/1012* (2013.01); *G01N 15/1425* (2013.01); *G01N 15/1429* (2013.01); *G01N 15/1459* (2013.01); *G01N 35/00623* (2013.01); *G01N 2015/1018* (2013.01); *G01N 2015/1068* (2013.01); *G01N 2015/1402* (2013.01); *G01N 2021/6439* (2013.01)

(58) Field of Classification Search
None
See application file for complete search history.

(56) References Cited

U.S. PATENT DOCUMENTS

| 9,075,005 | B2 | 7/2015 | Ebi et al. |
| 9,726,584 | B2 | 8/2017 | Yamada |
| 2007/0013906 | A1 | 1/2007 | Kawate |

(Continued)

FOREIGN PATENT DOCUMENTS

| CN | 1880942 A | 12/2006 |
| CN | 101685060 A | 3/2010 |

(Continued)

*Primary Examiner* — Robert T. Crow
(74) *Attorney, Agent, or Firm* — Brinks Gilson & Lione

(57) ABSTRACT

Disclosed is a method for determining abnormality in a particle analyzer. The method includes: staining first control particles but not staining second control particles which emit fluorescence; irradiating with light the first control particles and the second control particles flowing in a flow cell, and detecting fluorescence from the first control particles and the second control particles; obtaining a first management value indicating a detection result of the fluorescence emitted from the first control particles and a second management value indicating a detection result of the fluorescence emitted from the second control particles; and determining abnormality in the staining step, based on a value calculated from the first management value and the second management value or a ratio between the first management value and the second management value.

13 Claims, 12 Drawing Sheets

(56) References Cited

U.S. PATENT DOCUMENTS

| | | | |
|---|---|---|---|
| 2010/0183216 A1 | 7/2010 | Yamada | |
| 2012/0029934 A1 | 2/2012 | Shindo et al. | |
| 2013/0323825 A1* | 12/2013 | Sekino | ............... G01N 21/6486 |
| | | | 435/287.2 |

FOREIGN PATENT DOCUMENTS

| | | |
|---|---|---|
| CN | 101782524 A | 7/2010 |
| CN | 102375050 A | 3/2012 |
| CN | 103592262 A | 2/2014 |
| JP | 2007-047154 A | 2/2007 |
| JP | 2014-036618 A | 2/2014 |
| WO | WO 91/00509 A1 | 1/1991 |

* cited by examiner

FLOWCHART IN QUALITY CONTROL MODE

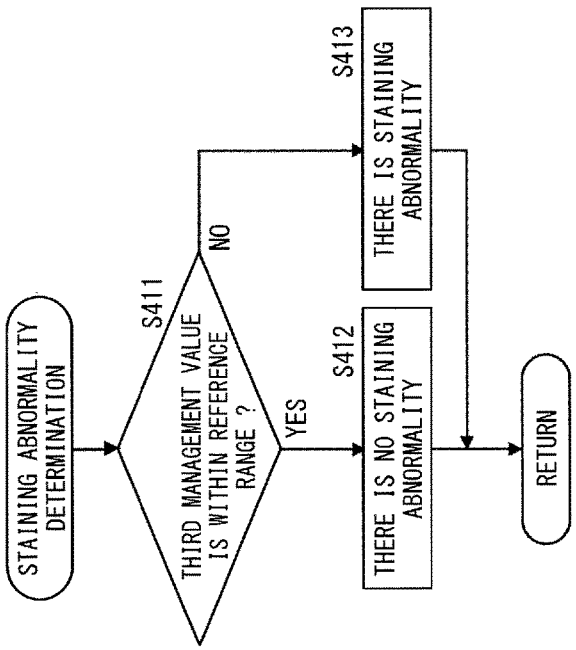
FIG. 7A
FIG. 7B
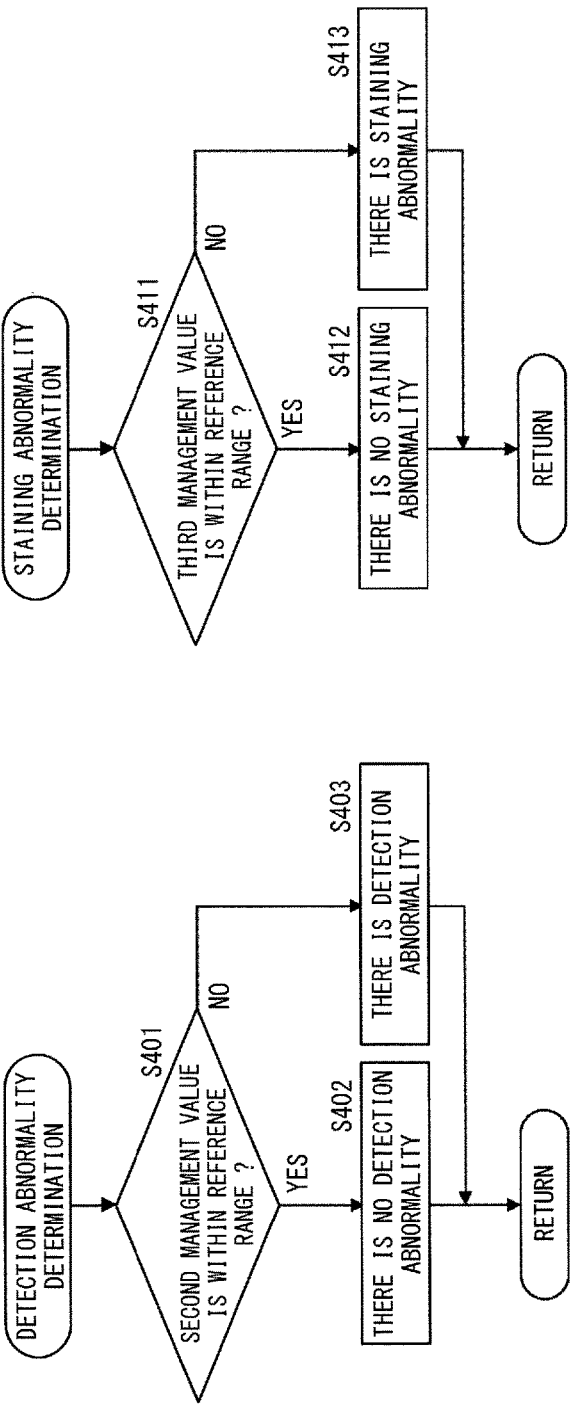
FIG. 7C  DETERMINATION THRESHOLD
| | SECOND MANAGEMENT VALUE | THIRD MANAGEMENT VALUE |
|---|---|---|
| UPPER LIMIT THRESHOLD | Sh22 | Sh32 |
| LOWER LIMIT THRESHOLD | Sh21 | Sh31 |

FIG. 9A

| FIRST MANAGEMENT VALUE | SECOND MANAGEMENT VALUE | THIRD MANAGEMENT VALUE |
|---|---|---|
| ... | ... | ... |

| DETECTION ABNORMALITY | NONE |
|---|---|
| STAINING ABNORMALITY | NONE |

FIG. 9B

| FIRST MANAGEMENT VALUE | SECOND MANAGEMENT VALUE | THIRD MANAGEMENT VALUE |
|---|---|---|
| ... | ... | ... |

| DETECTION ABNORMALITY | NONE |
|---|---|
| STAINING ABNORMALITY | PRESENT |

⚠ THERE IS ABNORMALITY IN STAINING PERFORMED IN SPECIMEN PREPARATION UNIT

PLEASE REPLACE REAGENT

FIG. 9C

| FIRST MANAGEMENT VALUE | SECOND MANAGEMENT VALUE | THIRD MANAGEMENT VALUE |
|---|---|---|
| ... | ... | ... |

| DETECTION ABNORMALITY | PRESENT |
|---|---|
| STAINING ABNORMALITY | NONE |

⚠ THERE IS ABNORMALITY IN OPTICAL DETECTION UNIT

PLEASE EXECUTE SENSITIVITY ADJUSTMENT

FIG. 12A  CONDITION 1

|  | FIRST MEASUREMENT VALUE | SECOND MEASUREMENT VALUE | VALUE OF RATIO |
|---|---|---|---|
| FIRST ROUND | 53763 | 304833 | 0.176 |
| SECOND ROUND | 53188 | 303711 | 0.175 |

|  | FIRST MANAGEMENT VALUE | SECOND MANAGEMENT VALUE | THIRD MANAGEMENT VALUE |
|---|---|---|---|
| AVERAGE VALUE | 53475 | 304297 | 0.176 |
| DETERMINATION | G | G | NG |

FIG. 12B  CONDITION 2

|  | FIRST MEASUREMENT VALUE | SECOND MEASUREMENT VALUE | VALUE OF RATIO |
|---|---|---|---|
| FIRST ROUND | 60088 | 348242 | 0.173 |
| SECOND ROUND | 57788 | 345898 | 0.167 |

|  | FIRST MANAGEMENT VALUE | SECOND MANAGEMENT VALUE | THIRD MANAGEMENT VALUE |
|---|---|---|---|
| AVERAGE VALUE | 58938 | 347070 | 0.170 |
| DETERMINATION | G | NG | NG |

FIG. 12C  CONDITION 3

|  | FIRST MEASUREMENT VALUE | SECOND MEASUREMENT VALUE | VALUE OF RATIO |
|---|---|---|---|
| FIRST ROUND | 59513 | 322461 | 0.185 |
| SECOND ROUND | 60088 | 322461 | 0.186 |

|  | FIRST MANAGEMENT VALUE | SECOND MANAGEMENT VALUE | THIRD MANAGEMENT VALUE |
|---|---|---|---|
| AVERAGE VALUE | 59800 | 322461 | 0.185 |
| DETERMINATION | G | NG | G |

FIG. 12D  DETERMINATION THRESHOLD

|  | FIRST MANAGEMENT VALUE | SECOND MANAGEMENT VALUE | THIRD MANAGEMENT VALUE |
|---|---|---|---|
| TARGET VALUE | 57000 | 307000 | 0.186 |
| TOLERANCE | 10.0% | 5.0% | 4.8% |
| UPPER LIMIT THRESHOLD | 62700 | 322350 | 0.195 |
| LOWER LIMIT THRESHOLD | 51300 | 291650 | 0.177 |

METHOD FOR DETERMINING ABNORMALITY IN PARTICLE ANALYZER AND PARTICLE ANALYZER

CROSS REFERENCE TO RELATED APPLICATION

This application claims priority from prior Japanese Patent Application No. 2014-202184, filed on Sep. 30, 2014, entitled "Method for determining abnormality in particle analyzer, method for performing quality control in analyzer, and particle analyzer", the entire content of which is incorporated herein by reference.

FIELD OF THE INVENTION

The present invention relates to a method for determining abnormality in a particle analyzer and a particle analyzer.

BACKGROUND

There are particle analyzers which analyze particles by detecting fluorescence generated from the particles. Such a particle analyzer mixes a sample containing particles with a fluorescent dye to prepare a measurement specimen, and causes the prepared measurement specimen to flow in a flow cell. The particle analyzer irradiates the flow of the measurement specimen with light, to detect fluorescence generated from each particle. Based on signals obtained through this detection, the particles are classified. In such a particle analyzer, in order to obtain an accurate measurement result, quality control using a quality control standard material is performed.

With the technique according to U.S. Patent Application Publication No. 2007/013906, the place of the abnormality occurring in the particle analyzer is determined by use of a quality control substance which contains: first standard particles to be fluorescence-stained by a first fluorescent dye; and second standard particles which contain a second fluorescent dye in advance and which are substantially not to be stained by the first fluorescent dye. When the measurement result of the second standard particles is outside a reference range, it is determined that abnormality is in the fluorescence detector. In the case where the measurement result of the second standard particle is within the reference range, when the measurement result of the first standard particle is outside a reference range, it is determined that abnormality is in the specimen preparation mechanism. In the case where the measurement result of the first standard particle is smaller than its reference range, and the measurement result of the second standard particle is greater than its reference range, it is determined that abnormality is in the specimen preparation mechanism and in the fluorescence detector.

SUMMARY OF THE INVENTION

The scope of the present invention is defined solely by the appended claims, and is not affected to any degree by the statements within this summary.

With the technique according to U.S. Patent Application Publication No. 2007/013906, there are cases whether abnormality is in the staining step or not cannot be discerned.

A first aspect of the present invention relates to a method for determining abnormality in a particle analyzer. The method includes: staining first control particles but not staining second control particles which emit fluorescence; irradiating with light the first control particles and the second control particles flowing in a flow cell, and detecting fluorescence from the first control particles and the second control particles; obtaining a first management value indicating a detection result of the fluorescence emitted from the first control particles and a second management value indicating a detection result of the fluorescence emitted from the second control particles; and determining abnormality in the staining step, based on a value calculated from the first management value and the second management value or a ratio between the first management value and the second management value.

A second aspect of the present invention relates to a method for determining abnormality in a particle analyzer which analyzes, based on a signal waveform of fluorescence emitted from a fluorescence-stained cell nucleus, an amount of DNA contained in the cell nucleus. The method includes: staining first control particles but not staining second control particles which emit fluorescence; irradiating with light the first control particles and the second control particles flowing in a flow cell, and obtaining signal waveforms based on the fluorescence from each first control particle and each second control particle; obtaining an area of the signal waveform of the fluorescence from each first control particle as a first fluorescence area; obtaining an area of the signal waveform of the fluorescence from each second control particle as a second fluorescence area; and determining abnormality in staining performed in the particle analyzer, based on the first fluorescence area and the second fluorescence area.

A third aspect of the present invention relates to a particle analyzer including: a specimen preparation unit configured to mix a specimen and a reagent which contains a fluorescent dye; an optical detection unit configured to cause the mixture prepared by the specimen preparation unit to flow in a flow cell, configured to irradiate with light the mixture flowing in the flow cell, and configured to detect light generated from the mixture as a result of the irradiation; and an analysis unit configured to analyze characteristic of light detected by the optical detection unit. When a quality control mode is set, the analysis unit is configured to cause the specimen preparation unit to mix the reagent, first control particles which are to be stained by the fluorescent dye, and second control particles which are not to be stained by the fluorescent dye and which emit fluorescence, to prepare a mixture, cause the optical detection unit: to cause the mixture to flow in the flow cell; to irradiate with light the first control particles and the second control particles flowing in the flow cell; and to detect fluorescence from the first control particles and the second control particles, obtain a first management value indicating a detection result of the fluorescence emitted from the first control particles and a second management value indicating a detection result of the fluorescence emitted from the second control particles, and determine abnormality in staining performed in the specimen preparation unit, based on a value calculated from the first management value and the second management value or a ratio between the first management value and the second management value.

The effects and the significance of the present invention will be further clarified by the description of the embodiments below. However, the embodiments below are merely examples for implementing the present invention, and the present invention is not limited to the embodiments below by any degree.

BRIEF DESCRIPTION OF THE DRAWINGS

FIG. 7A is a flow chart showing detection abnormality determination according to Embodiment 1;

FIG. 7B is a flow chart showing staining abnormality determination according to Embodiment 1;

FIG. 7C shows lower limit thresholds and upper limit thresholds to be used in determination according to Embodiment 1;

FIG. 9A shows a screen to be displayed on an output unit according to Embodiment 1;

FIG. 9B shows a screen to be displayed on the output unit according to Embodiment 1;

FIG. 9C shows a screen to be displayed on the output unit according to Embodiment 1;

FIG. 12A shows first measurement value, second measurement value, first management value, second management value, and third management value obtained under Condition 1 as well as determination result, in an experiment according to Embodiment 1;

FIG. 12B shows first measurement value, second measurement value, first management value, second management value, and third management value obtained under Condition 2 as well as determination result, in an experiment according to Embodiment 1;

FIG. 12C shows first measurement value, second measurement value, first management value, second management value, and third management value obtained under Condition 3 as well as determination result, in an experiment according to Embodiment 1; and FIG. 12D shows lower limit thresholds and upper limit thresholds used in the determination made in the experiment according to Embodiment 1.

DETAILED DESCRIPTION OF THE PREFERRED EMBODIMENTS

Embodiments 1 and 2 below are applied to an apparatus whose analysis target is uterine cervix cells and which obtains information regarding canceration of the cells. The analysis target may be buccal cells, epithelial cells of the bladder, the pharynx, or the like, or epithelial cells of organs.

Embodiment 1

Figure 1:
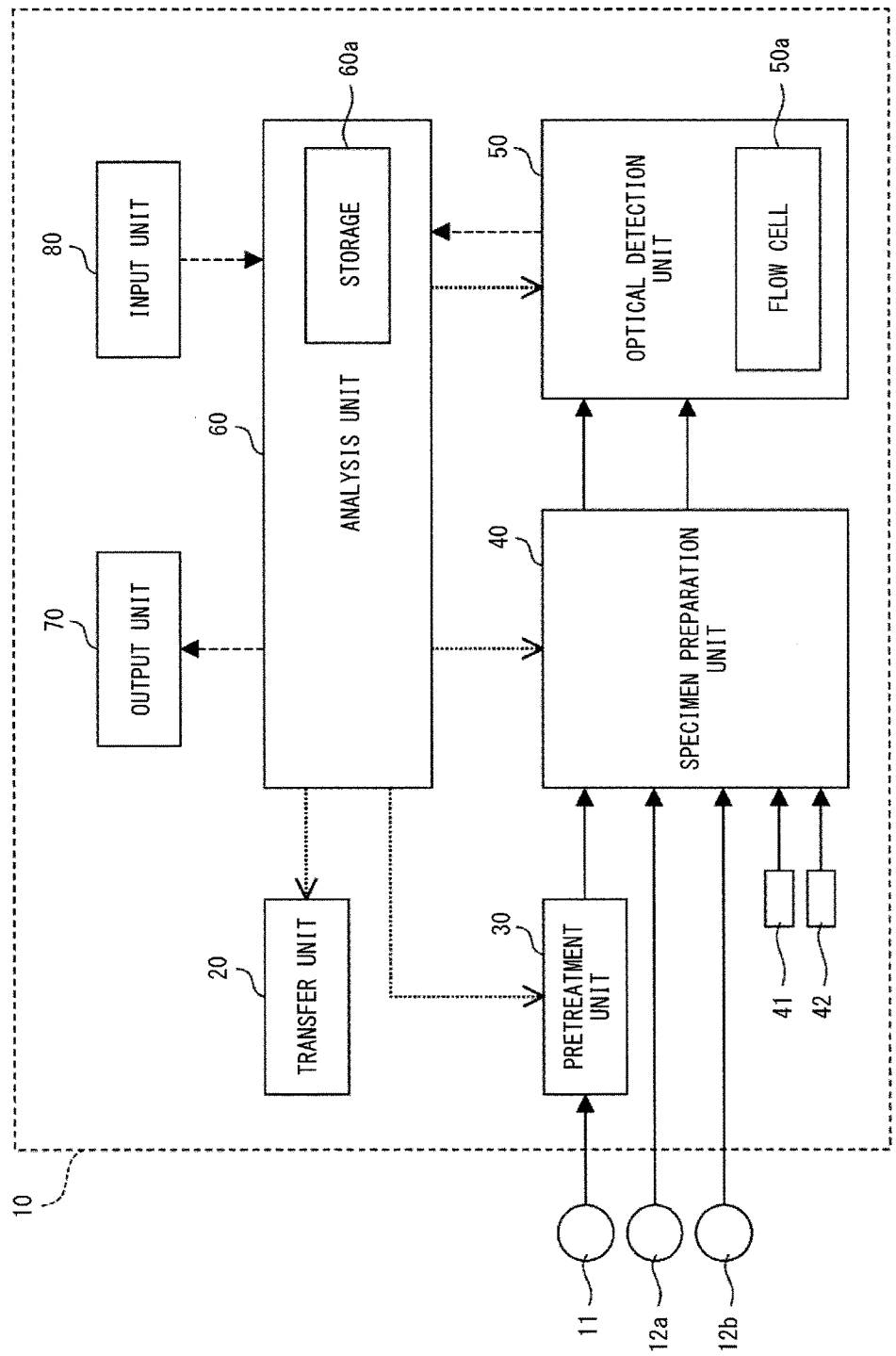
FIG. 1 is a block diagram showing a configuration of a particle analyzer according to Embodiment 1.

As shown in FIG. 1, a particle analyzer 10 includes a transfer unit 20, a pretreatment unit 30, a specimen preparation unit 40, an optical detection unit 50, an analysis unit 60, an output unit 70, and an input unit 80. The particle analyzer 10 has a normal mode and a quality control mode as operation modes. The particle analyzer 10 analyzes a sample 11 in the normal mode. The sample 11 is a clinical sample which is collected from the uterine cervix of a subject, and contains epithelial cells of the uterine cervix. In the quality control mode, the particle analyzer 10 performs quality control by use of first control particles 12a and second control particles 12b.

First, a case where the operation mode is the normal mode will be described. The sample 11 is a liquid in which cells are suspended in a preservative liquid whose principal component is alcohol. The sample 11 is contained in a sample container. Preferably, the alcohol is methanol. The transfer unit 20 aspirates the sample 11, dispenses the aspirated sample 11 into a cuvette not shown, and transfers the cuvette. The pretreatment unit 30 disperses, with ultrasonic waves, aggregated cells contained in the sample 11 dispensed in the cuvette. Further, the pretreatment unit 30 replaces the preservative liquid suspending the cells contained in the sample 11, with a diluent. The pretreatment unit 30 removes contaminant from the sample 11 and concentrates the sample 11.

The specimen preparation unit 40 mixes reagents 41 and 42 and the sample 11 having been subjected to the processing by the pretreatment unit 30, to prepare a mixture. The reagent 41 contains a fluorescent dye. The fluorescent dye contained in the reagent 41 is a nucleic acid staining dye. Nucleic acid in each cell contained in the sample 11 is stained by the reagent 41.

It is sufficient that the nucleic acid staining dye is a fluorescent dye which emits fluorescence by binding to nucleic acid. An example of the nucleic acid fluorescent dye is propidium iodide, ethidium bromide, ethidium-acridine heterodimer, ethidium diazide, ethidium homodimer-1, ethidium homodimer-2, ethidium monoazide, trimethylenebis[[3-[[4-[[(3-methyl benzothiazole-3-ium)-2-yl]methylene]-1,4-dihydroquinoline]-1-yl]propyl]dimethylaminium] tetraiodide, 4-[(3-methylbenzothiazole-2(3H)-ylidene) methyl]-1-[3-(trimethylaminio) propyl]quinolinium diiodide, N,N,N',N'-tetramethyl-N,N'-bis[3-[4-[3-[(3-methylbenzothiazole-3-ium)-2-yl]-2-propenylidene]-1,4-dihydroquinoline-1-yl]propyl]-1,3-propanediaminium tetraiodide, or 2-[3-[[1-[3-(trimethylaminio) propyl]-1,4-dihydroquinoline]-4-ylidene]-1-propenyl]-3-methylbenzothiazol-3-ium diiodide.

The reagent 42 contains an RNA remover for removing RNA contained in the sample 11. The sample 11 sometimes contains RNA in the cells. Since the reagent 41 is a nucleic acid staining dye, there are cases where the reagent 41 stains RNA contained in the sample 11. When RNA is stained, RNA-derived fluorescence is added to DNA-derived fluorescence to be detected, causing increased background, which is not preferable. Such RNA is degraded by the reagent 42.

The optical detection unit 50 includes a flow cytometer. The optical detection unit 50 causes the mixture prepared by the specimen preparation unit 40 to flow in a flow cell 50a. The optical detection unit 50 irradiates with light the mixture flowing in the flow cell 50a. The optical detection unit 50 detects light emitted from the mixture.

Figure 2A:
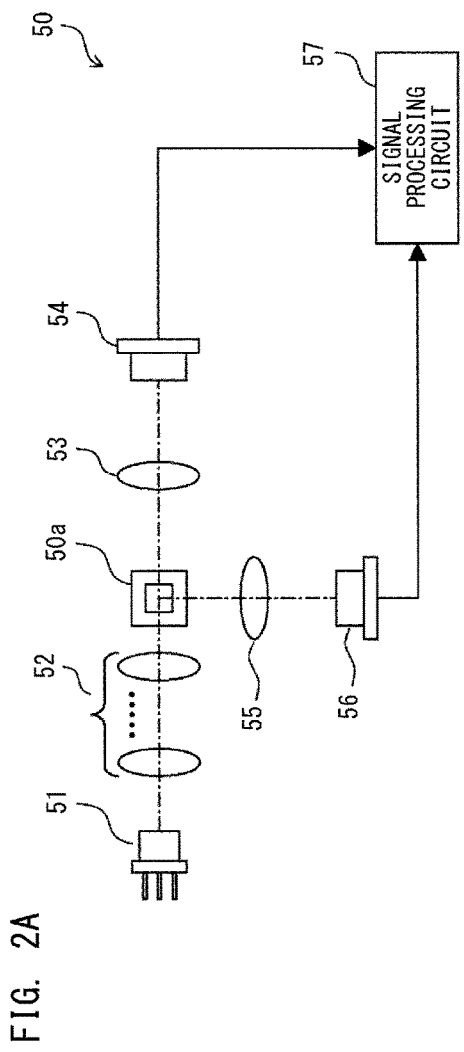
FIG. 2A is a schematic diagram showing a configuration of an optical detection unit according to Embodiment 1.

As shown in FIG. 2A, the optical detection unit 50 includes the flow cell 50a, a light source 51, a condenser lens group 52, a condenser lens 53, an optical detector 54, a condenser lens 55, an optical detector 56, and a signal processing circuit 57.

The light source 51 emits a laser beam. The condenser lens group 52 is composed of a plurality of lenses. The condenser lens group 52 condenses the laser beam on the mixture flowing in the flow cell 50a. Accordingly, from the particles in the mixture, forward scattered light and fluorescence are generated. Forward scattered light reflects the size of each particle, and fluorescence reflects the degree of staining of the particle.

The condenser lens 53 condenses forward scattered light. The optical detector 54 receives forward scattered light. The optical detector 54 is a photodiode. The optical detector 54 outputs an electric signal corresponding to the received forward scattered light, i.e., a forward scattered light signal. The condenser lens 55 condenses fluorescence. The optical detector 56 receives fluorescence. The optical detector 56 is a photomultiplier. The optical detector 56 outputs an electric signal corresponding to the received fluorescence, i.e., a fluorescence signal.

Figure 2D:
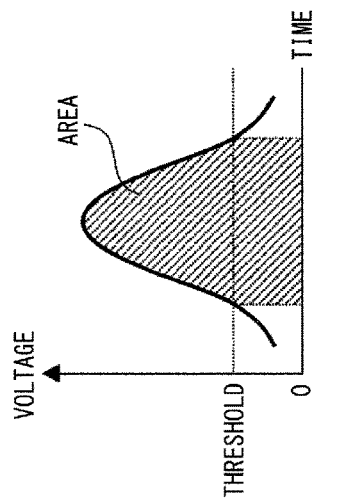
FIG. 2D is a schematic diagram showing a characteristic parameter according to Embodiment 1.
Figure 2C:
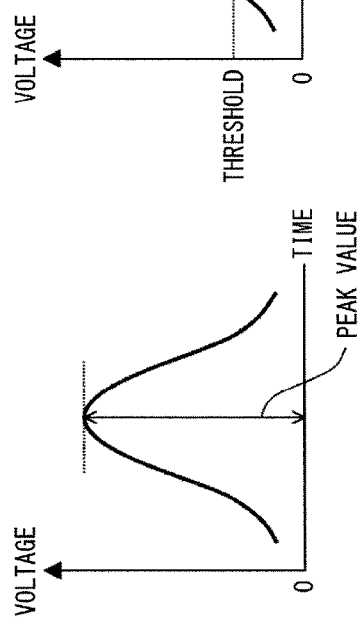
FIG. 2C is a schematic diagram showing a characteristic parameter according to Embodiment 1.
Figure 2B:
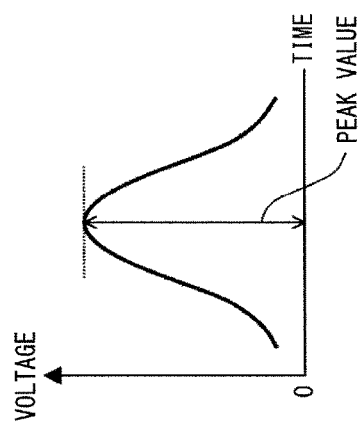
FIG. 2B is a schematic diagram showing a characteristic parameter according to Embodiment 1.

The signal processing circuit 57 performs predetermined signal processing on signals outputted from the optical detectors 54 and 56, to obtain waveforms corresponding to the forward scattered light signal and the fluorescence signal, respectively. The signal processing circuit 57 calculates a plurality of characteristic parameters such as the peak value, the width, and the area, from each obtained waveform. As shown in FIG. 2B, the peak value is the maximum value of the waveform. As shown in FIG. 2C, the width is the width of the portion, of the waveform, that is greater than a predetermined threshold. As shown in FIG. 2D, the area is the area of the portion surrounded by the waveform and line segments which are extended downwardly from the points where a predetermined threshold crosses the waveform. The signal processing circuit 57 outputs characteristic parameters of each light of each particle, to the analysis unit 60.

With reference back to FIG. 1, the analysis unit 60 includes a CPU. As indicated by dotted lines, the analysis unit 60 controls the transfer unit 20, the pretreatment unit 30, the specimen preparation unit 40, and the optical detection unit 50. The analysis unit 60 stores, in a storage 60a, characteristic parameters of each light of each particle outputted from the signal processing circuit 57. The analysis unit 60 analyzes characteristics of each light based on the characteristic parameters of each light of each particle, to obtain an analysis result. The analysis result includes information regarding canceration, and the like. The analysis unit 60 displays the analysis result on the output unit 70. The analysis unit 60 receives instructions from an operator via the input unit 80. The output unit 70 is a display. The input unit 80 is a mouse and/or a key board.

Next, a case where the operation mode is the quality control mode will be described. The first control particles 12a are particles to be stained by the fluorescent dye of the reagent 41. The second control particles 12b are particles which are substantially not stained by the fluorescent dye of the reagent 41, and which emit fluorescence by containing a fluorescent dye in advance.

The first control particles 12a are selected from the group consisting of: cells, polyacrylamide particles, hydrophilic vinyl polymer particles, latex particles, and silica particles. Preferably, the first control particles 12a are cells.

The second control particles 12b are fluorescent latex particles. The second control particles 12b emit fluorescence more intense than that emitted by the first control particles 12a. More specifically, the second control particles 12b emit fluorescence more intense than that emitted by the first control particles 12a which have been stained under an appropriate condition by use of the reagents 41 and 42. Thus, based on the difference between the fluorescence intensities, the first control particles 12a can be distinguished from the second control particles 12b.

The first control particles 12a and the second control particles 12b are contained in containers, respectively. The transfer unit 20 aspirates the first control particles 12a and the second control particles 12b, dispenses them into cuvettes not shown, and transfers the cuvettes. The pretreatment unit 30 is not used in the quality control mode. The specimen preparation unit 40 mixes the first control particles 12a, the second control particles 12b, and the reagents 41 and 42, to prepare a mixture. Accordingly, the first control particles 12a are stained by the reagent 41.

The first control particles 12a contain RNA in the specimen. This is for determining whether the reagent 42 containing the RNA remover is properly acting or not.

As in the normal mode, the optical detection unit 50 causes the mixture prepared by the specimen preparation unit 40 to flow in the flow cell 50a. The optical detection unit 50 irradiates with light the first control particles 12a and the second control particles 12b flowing in the flow cell 50a. The optical detection unit 50 detects light emitted from each of the first control particles 12a and the second control particles 12b. The signal processing circuit 57 of the optical detection unit 50 outputs, to the analysis unit 60, characteristic parameters of each light of each particle. The analysis unit 60 stores, in the storage 60a, the characteristic parameters of each light of each particle outputted from the signal processing circuit 57.

Based on the characteristic parameters of each light of each particle, the analysis unit 60 obtains a first management value, a second management value, and a third management value. The first management value and the second management value represent detection results of fluorescence emitted from the first control particles 12a and the second control particles 12b, respectively. The third management value is a value calculated from the first management value and the second management value. Based on the second management value, the analysis unit 60 determines detection abnormality, i.e., abnormality in the optical detection unit 50. Based on the third management value, the analysis unit 60 determines staining abnormality, i.e., abnormality in staining performed in the specimen preparation unit 40. When there are detection abnormality and staining abnormality, the analysis unit 60 outputs notifications of the respective detection abnormality and staining abnormality via the output unit 70. How to determine detection abnormality and staining abnormality will be described later with reference to flow charts.

Next, the process performed by the particle analyzer 10 in the normal mode will be described with reference to the flow chart shown in FIG. 3.

Figure 3:
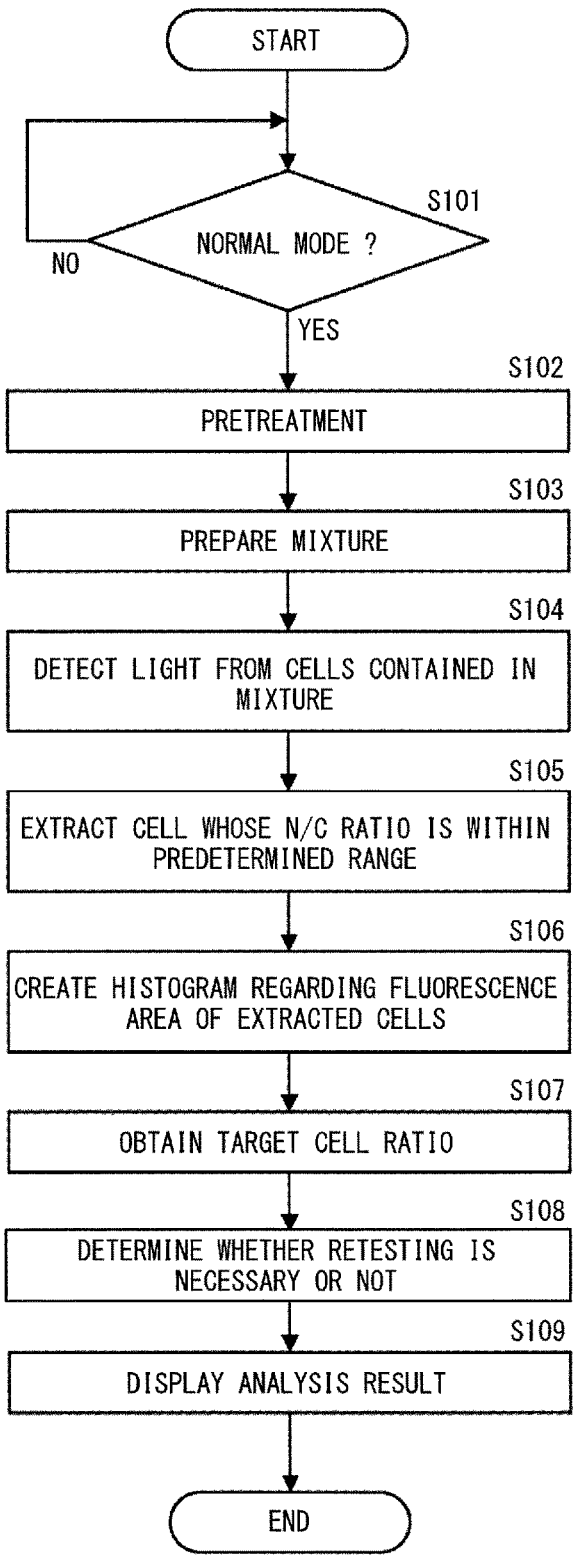
FIG. 3 is a flow chart showing a process performed by the particle analyzer in a normal mode according to Embodiment 1.

As shown in FIG. 3, upon activation of the particle analyzer 10, in step S101, the analysis unit 60 determines whether the operation mode has been set to the normal mode via the input unit 80 by an operator. When having determined as YES in step S101, then in step S102, the analysis unit 60 causes the pretreatment unit 30 to perform pretreatment on the sample 11 as described above. In step S103, the analysis unit 60 causes the specimen preparation unit 40 to mix the reagents 41 and 42 and the sample 11 having been subjected to the processing by the pretreatment unit 30, to prepare a mixture. In step S104, the analysis unit 60 causes the optical detection unit 50: to cause the mixture to flow in the flow cell 50a; to irradiate with light the mixture flowing in the flow cell 50a; and to detect light generated from the mixture as a result of the irradiation. The analysis unit 60 stores, in the storage 60a, characteristic parameters of each light generated from each cell contained in the mixture.

In step S105, based on the characteristic parameters of each light of each particle stored in the storage 60a, the analysis unit 60 extracts cells whose N/C ratio is within a predetermined range from among all the cells contained in the mixture. By calculating "the width of the waveform of a fluorescence signal/the width of the waveform of a forward scattered light signal", the analysis unit 60 obtains the N/C ratio. Instead of the N/C ratio, the analysis unit 60 may calculate the C/N ratio, and may extracts cells whose C/N ratio is within a predetermined range.

Next, in step S106 and S107, the analysis unit 60 performs analysis based on the amount of DNA of each of cells contained in the sample 11 as described below. In step S106, the analysis unit 60 creates a histogram regarding the amount of DNA of the cells extracted in step S105. Specifically, the analysis unit 60 creates a histogram whose two axes represent the area of waveform of fluorescence signal and the number of cells. The area of the waveform of a fluorescence signal (hereinafter, referred to as "fluorescence area") corresponds to the amount of DNA of the cell. In step S107, the analysis unit 60 analyses the fluorescence areas of the cells contained in the sample 11, to obtain the ratio of cells each containing a predetermined amount or more of DNA (hereinafter, referred to as "target cell ratio"). Specifically, based on the histogram created in step S106, the analysis unit 60 calculates "the number of cells each having a fluorescence area greater than or equal to a predetermined threshold/the number of cells each having a fluorescence area less than the predetermined threshold", to obtain a target cell ratio.

Here, for convenience of explanation, the target cell ratio is obtained by creating a histogram in step S106, but it is not necessary to actually create a histogram. That is, the target cell ratio may be obtained through data processing based on the cells extracted in step S105. Similarly, also in step S204 in FIG. 4, a first measurement value and a second measurement value may be obtained through data processing without creating a histogram.

In step S108, based on the target cell ratio obtained in step S107, the analysis unit 60 determines whether retesting is necessary or not. When the target cell ratio is greater than or equal to a predetermined value, the analysis unit 60 determines that retesting is necessary. When the target cell ratio is less than the predetermined value, the analysis unit 60 determines that retesting is not necessary. In step S109, the analysis unit 60 displays, on the output unit 70, the target cell ratio and the determination result indicating whether retesting is necessary or not, as the analysis result.

In the particle analyzer 10 which performs analysis based on the amount of DNA, staining of nucleic acid by the reagent 41 and reduced background by the reagent 42 have direct influence on the shape of the histogram regarding the amount of DNA. The reagent 41 and the reagent 42 may deteriorate due to storage condition and use condition. When the reagent 41 is deteriorated, nucleic acid is not sufficiently stained. This may case the distribution of the histogram to be shifted toward the low value side. When the reagent 42 is deteriorated, RNA is not sufficiently removed, and background of fluorescence is increased. This may cause the distribution of the histogram to be shifted toward the high value side. Either case could have unfavorable influence on accurate analysis of the amount of DNA.

Therefore, quality management of the reagents 41 and 42 is important, and further, it is important to determine staining abnormality in the specimen preparation unit 40 in the quality control mode.

Next, the process performed by the particle analyzer 10 in the quality control mode will be described with reference to the flow chart shown in FIG. 4.

Figure 4:
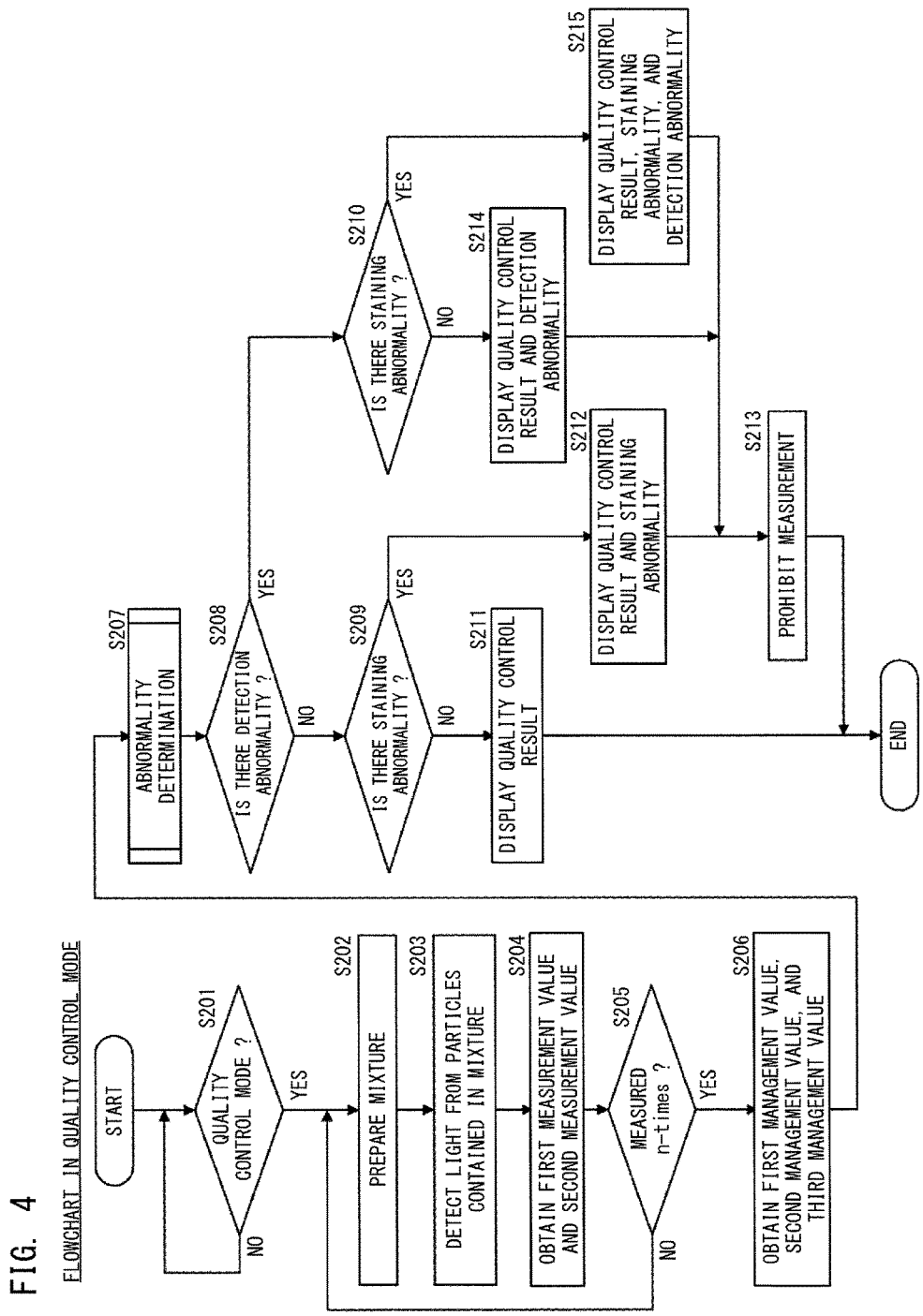
FIG. 4 is a flow chart showing a process performed by the particle analyzer in a quality control mode according to Embodiment 1.

As shown in FIG. 4, upon activation of the particle analyzer 10, in step S201, the analysis unit 60 determines whether the operation mode has been set to the quality control mode via the input unit 80 by the operator. When having determined as YES in step S201, then, in step S202, the analysis unit 60 causes the specimen preparation unit 40 to mix the reagents 41 and 42, the first control particles 12a, and the second control particles 12b, to prepare a mixture. In step S203, the analysis unit 60 causes the optical detection unit 50: to cause the mixture to flow in the flow cell 50a; to irradiate with light the first control particles 12a and the second control particles 12b flowing in the flow cell 50a; and to detect fluorescence from the first control particles 12a and the second control particles 12b. The analysis unit 60 stores, in the storage 60a, characteristic parameters of each light generated from the first control particles 12a and characteristic parameters of each light generated from the second control particles 12b.

In step S204, the analysis unit 60 obtains a first measurement value and a second measurement value. Specifically, first, based on the difference in fluorescence intensities, the analysis unit 60 classifies data of each particle stored in the storage 60a, as either the first control particle 12a or the second control particle 12b. As described above, the second control particles 12b emit fluorescence more intense than that emitted by the first control particles 12a. Therefore, based on the difference in fluorescence intensities, classification between the first control particles 12a and the second control particles 12b can be performed.

Figure 5:
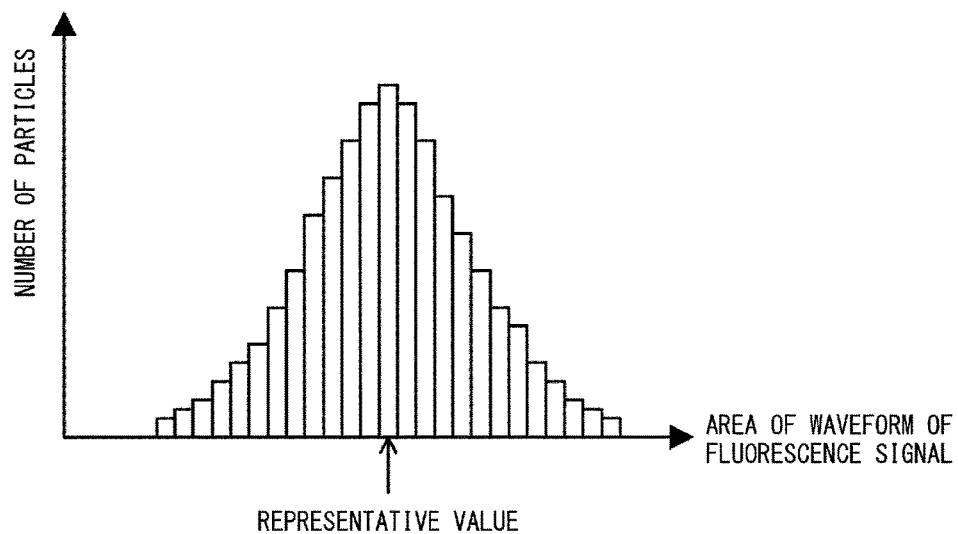
FIG. 5A is a schematic diagram showing a histogram regarding the area of the waveform of a fluorescence signal generated from each particle according to Embodiment 1.
FIG. 5B shows first measurement value and second measurement value according to Embodiment 1.

Next, with respect to each type of the first control particles 12a and the second control particles 12b, as shown in FIG. 5A, the analysis unit 60 creates a histogram regarding the fluorescence area generated from each particle. The analysis unit 60 obtains a representative value in the histogram as shown in FIG. 5A. The representative value is the most frequent value, i.e., the fluorescence area which appears most frequently in the histogram regarding the fluorescence area. The representative value may be an average value or a median. The analysis unit 60 sets the representative value obtained based on the histogram of the first control particles 12a, as the first measurement value. The analysis unit 60 sets the representative value obtained based on the histogram of the second control particles 12b, as the second measurement value.

In step S205, based on a predetermined number of times of measurements, the analysis unit 60 determines whether the quality control measurement has ended. When it is assumed that the predetermined number of times of measurements is n, the analysis unit 60 repeats the processes of steps S202 to S204 n times. When it is assumed that the n-th first measurement value is V1n and the n-th second measurement value is V2n, the analysis unit 60 obtains a first measurement value and a second measurement value in each of the first to n-th measurements as shown in FIG. 5B. The number n is set to 1 or 2, for example.

In the above procedure, the reagents 41 and 42, the first control particles 12a, and the second control particles 12b are mixed together to prepare a mixture. However, instead of this, a mixture of the first control particles 12a and a mixture of the second control particles 12b may be separately prepared. In this case, the processes of steps S202 to S205 are replaced with steps S221 to S228, as shown in FIG. 6.

Figure 6:
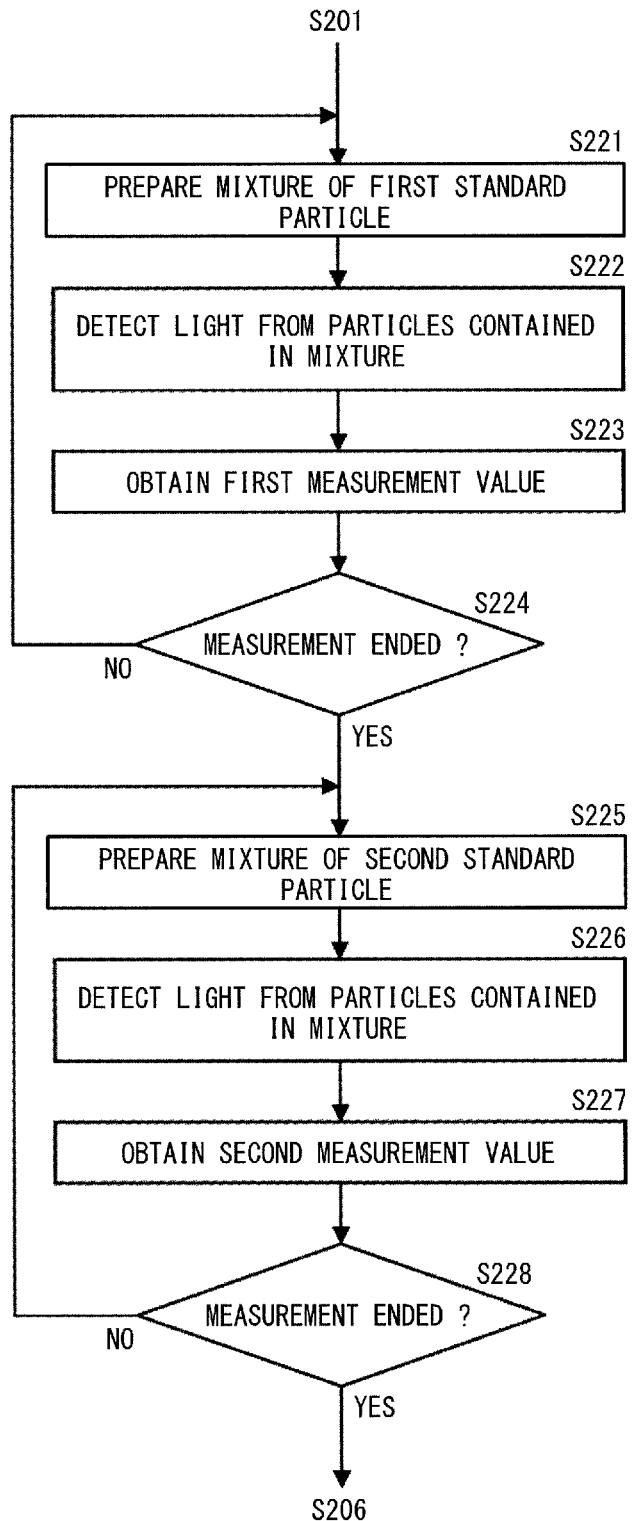
FIG. 6 is a modification of the flow chart showing a process performed by the particle analyzer in the quality control mode according to Embodiment 1.

As shown in FIG. 6, in step S221, the analysis unit 60 causes the specimen preparation unit 40 to mix the reagents 41 and 42 and the first control particles 12a, to prepare a mixture. In step S222, the analysis unit 60 causes the optical detection unit 50: to cause the mixture to flow in the flow cell 50a; to irradiate with light the first control particles 12a flowing in the flow cell 50a; and to detect fluorescence from the first control particles 12a. In step S223, the analysis unit 60 obtains a first measurement value, as in step S204 above. In accordance with the determination in step S224, the analysis unit 60 repeats the processes of S221 to S223 the predetermined number of times, to obtain the first measurement values the predetermined number of times.

Next, in steps S225 to S228, as in steps S221 to S224, the analysis unit 60 obtains the second measurement values the predetermined number of times. Also through steps S221 to S228 in FIG. 6, as in steps S202 to S205 in FIG. 4, the first measurement values and the second measurement values are obtained as shown in FIG. 5B.

With reference back to FIG. 4, in step S206, the analysis unit 60 obtains a first management value, a second management value, and a third management value. The first management value is the average of the first measurement values obtained in step S204. The first management value is obtained by Expression (11) below. The second management value is the average of the second measurement values obtained in step S204. The second management value is obtained by Expression (12) below. The third management value is a value calculated from the first management value and the second management value. Preferably, the third management value is a value of the ratio of the first management value to the second management value. The third management value is obtained by Expression (13) below.

First management value=$(V11+V12+ \ldots +V1n)/n$ (11)

Second management value=$(V21+V22+ \ldots +V2n)/n$ (12)

Third management value=first management value/
second management value (13)

The second management value is a value obtained based on fluorescence generated from the second control particles 12b which are substantially not stained by the reagent 41 and which contain a fluorescent dye in advance. Thus, the second management value reflects the state of the optical detection unit 50. In contrast, the first management value is a value that also reflects the state (such as reagent deterioration) of the staining step in addition to the state of the optical detection unit 50. The first management value can be considered as the product of the second management value representing the state of the optical detection unit 50 and the value representing the state of the staining step. Therefore, the third management value obtained by dividing the first management value by the second management value reflects the state of the staining step.

The third management value may be a value obtained by squaring the first management value/the second management value. The third management value may be a value obtained by adding a constant to the first management value/the second management value, subtracting a constant from the first management value/the second management value, multiplying the first management value/the second management value with a constant, or dividing the first management value/the second management value by a constant. The third management value may be the second management value/the first management value. The third management value may be a value of a log of the first management value/the second management value. The third management value may be obtained by $(V11+V12+ \ldots + V1n)/(V21+V22+ \ldots +V2n)$, without using the first management value and the second management value. The third management value may not be a value based on the ratio between the first management value and the second management value. For example, the ratio of the first management value to a target value 1 of the first management value (first management value/target value 1) and the ratio of the second management value to a target value 2 of the second management value (second management value/target value 2) are calculated, and then, the difference between these ratios may be used as the third management value.

In step S207, based on the second management value and the third management value, the analysis unit 60 performs the processes of abnormality determinations shown in FIGS. 7A and 7B in parallel.

As shown in FIG. 7A, in step S401, the analysis unit 60 determines whether the second management value is within a reference range. As shown in FIG. 7C, the reference range of the second management value is defined by a lower limit threshold Sh21 and an upper limit threshold Sh22. The lower limit threshold Sh21 and the upper limit threshold Sh22 are stored in the storage 60a. When having determined as YES in step S401, then, in step S402, the analysis unit 60 determines that there is no detection abnormality. When having determined as NO in step S401, then, in step S403, the analysis unit 60 determines that there is detection abnormality.

As shown in FIG. 7B, in step S411, the analysis unit 60 determines whether the third management value is within a reference range. As shown in FIG. 7C, the reference range of the third management value is defined by a lower limit threshold Sh31 and an upper limit threshold Sh32. The lower limit threshold Sh31 and the upper limit threshold Sh32 are stored in the storage 60a. When having determined as YES in step S411, then, in step S412, the analysis unit 60 determines that there is no staining abnormality. When having determined as NO in step S411, then, in step S413, the analysis unit 60 determines that there is staining abnormality.

Figure 8B:
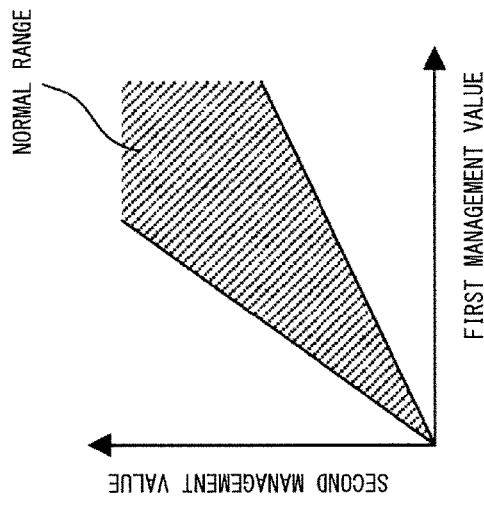
FIG. 8B shows a normal range to be used in the staining abnormality determination according to the modification.
Figure 8A:
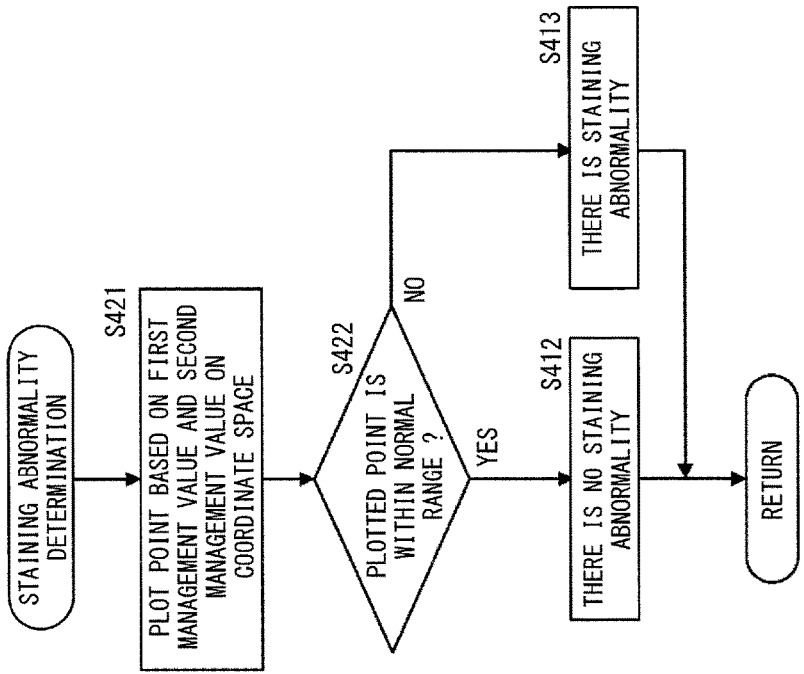
FIG. 8A is a modification of the flow chart showing the staining abnormality determination according to Embodiment 1.

The staining abnormality determination may be a process shown in FIG. 8A, instead of the process shown in FIG. 7B. In this case, as shown below, determination of staining abnormality is performed based on the ratio between the first management value and the second management value. Thus, there is no need to obtain the third management value in step S206 in FIG. 4. Compared with the process the FIG. 7B, in the process shown in FIG. 8A, step S421 is added before step S411, and step S411 is replaced with step S422.

As shown in FIG. 8A, in step S421, the analysis unit 60 plots a point based on the obtained first management value and second management value, on a coordinate space having axes which represent first management value and second management value. In the coordinate space, a normal range is set as indicated by diagonal lines in FIG. 8B. The analysis unit 60 has the normal range stored in the storage 60a in advance. In step S422, the analysis unit 60 determines whether the plotted point is in the normal range. When having determined as YES in step S422, then, in step S412, the analysis unit 60 determines that there is no staining abnormality. When having determined as NO in step S422, then, in step S413, the analysis unit 60 determines that there is staining abnormality.

Here, for convenience of explanation, in step S421, a point based on the first management value and the second management value is plotted on the coordinate space, but it is not necessary to actually create the coordinate space and plot the point. That is, instead of creating the coordinate space, plotting the point, and determining whether the plotted point is within the normal range, whether the point based on the first management value and the second management value is within the normal range may be determined by data processing.

The process of abnormality determination is performed in accordance with separate flow charts as shown in FIGS. 7A and 7B. However, the flow charts shown in FIGS. 7A and 7B may be combined into one flow chart, and in accordance with the one flow chart, a process of determining system abnormality, a process of determining detection abnormality, and a process of determining staining abnormality may be performed.

With reference back to FIG. 4, when all the processes of abnormality determination shown in FIGS. 7A and 7B have ended, then, in step S208, the analysis unit 60 determines the presence/absence of detection abnormality based on the result of the process shown in FIG. 7A. In steps S209 and S210, the analysis unit 60 determines the presence/absence of staining abnormality based on the result of the process shown in FIG. 7B.

When having determined as NO in step S208 and having determined as NO in step S209, then, in step S211, the analysis unit 60 displays a screen 71 as shown in FIG. 9A on the output unit 70. The screen 71 includes lists 71a and 71b showing quality control results. The list 71a displays the first to third management values in the form of a list. The list 71b displays, as a quality control abnormality determination result, the presence/absence of detection abnormality and the presence/absence of staining abnormality in the form of a list.

When having determined as NO in step S208 and having determined as YES in step S209, then, in step S212, the analysis unit 60 displays a screen 72 as shown in FIG. 9B on the output unit 70. The screen 72 includes lists 72a and 72b similar to the lists 71a and 71b shown in FIG. 9A. Further, the screen 72 includes a region 72c and a message "There is abnormality in staining performed in the specimen preparation unit". In the region 72c, "Please replace reagent" as a message for urging replacement of the reagent 41, 42 is displayed. The message displayed in the region 72c may be "Please confirm the state of reagent", or "Please contact a service person". By referring to the screen 72, the operator can know that there is abnormality in staining performed in the specimen preparation unit 40. By referring to the region 72c, the operator can smoothly and quickly take measures for eliminating the staining abnormality. Thus, the operator can smoothly and quickly eliminate the staining abnormality.

In step S213, the analysis unit 60 prohibits measurement on the sample 11 in the normal mode. Accordingly, the processes of step S102 and thereafter in FIG. 3 are not started. Therefore, it is possible to prevent measurement on the sample 11 from being mistakenly performed in the normal mode, and thus it is possible to prevent an analysis result of low accuracy from being obtained. In the case where measurement on the sample 11 has been prohibited in step S212, the process of the quality control mode shown in FIG. 4 is performed again after the operator or a service person has taken measures. At this time, when having determined as NO in step S208 and having determined as NO in step S209, the analysis unit 60 cancels the prohibition of measurement on the sample 11.

When having determined as YES in step S208 and having determined as NO in step S210, then, in step S214, the analysis unit 60 displays a screen 73 as shown in FIG. 9C on the output unit 70. Then, in step S213, the analysis unit 60 prohibits measurement on the sample 11 in the normal mode. The screen 73 includes lists 73a and 73b similar to the lists 71a and 71b shown in FIG. 9A. Further, the screen 73 includes a region 73c and a message "There is abnormality in the optical detection unit". In the region 73c, "Please execute sensitivity adjustment." is displayed as a message for urging taking measures. The message displayed in the region 73c may be "Please contact a service person". By referring to the screen 73, the operator can know that there is abnormality in the optical detection unit 50. By referring to the region 73c, the operator can smoothly and quickly take measures for eliminating the detection abnormality. Thus, the operator can smoothly and quickly eliminate the detection abnormality.

Figure 10A:
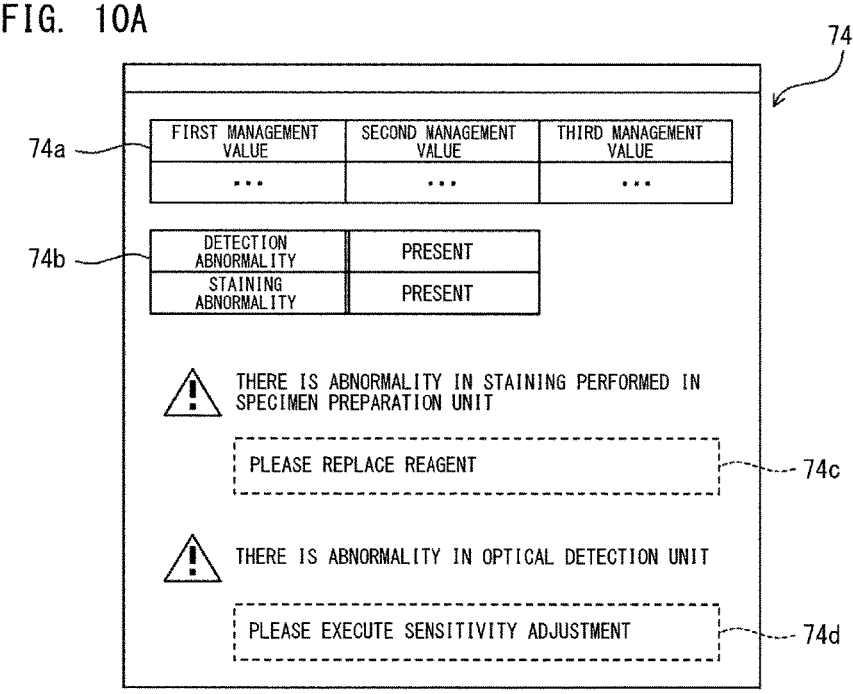
FIG. 10A shows a screen to be displayed on the output unit according to Embodiment 1.

When having determined as YES in step S208 and having determined as YES in step S210, then, in step S215, the analysis unit 60 displays a screen 74 as shown in FIG. 10A on the output unit 70. Then, in step S213, the analysis unit 60 prohibits measurement on the sample 11 in the normal mode. The screen 74 includes lists 74a and 74b similar to the lists 71a and 71b shown in FIG. 9A. Further, similarly to the screen 72 in FIG. 9B, the screen 74 includes a message and a region 74c. Further, similarly to the screen 73 in FIG. 9C, the screen 74 includes a message and a region 74d.

In step S215, even in the case where there is abnormality in both the optical detection unit 50 and the specimen preparation unit 40, notifications of detection abnormality and reagent abnormality are individually and assuredly made. Accordingly, the operator can smoothly and quickly take measures for eliminating the abnormalities, and thus, the operator can smoothly and quickly eliminate the detection abnormality and the reagent abnormality.

Figure 10B:
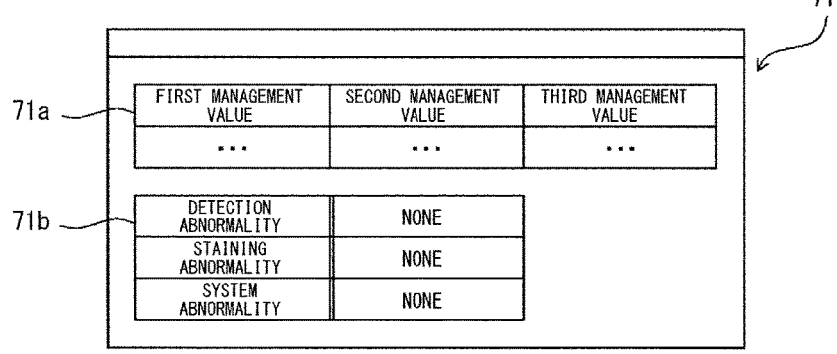
FIG. 10B shows a modification of the screen to be displayed on the output unit according to Embodiment 1.

FIG. 10B shows another example of the screen 71 showing a quality control result. On the screen 71 shown in FIG. 10B, the list 71b displays the presence/absence of system abnormality. System abnormality is an integrated result of the determination on detection abnormality and the determination on staining abnormality. Therefore, when abnormality is determined to be present in either detection or staining, the list 71b displays "System abnormality: present". When there is abnormality in neither detection nor staining, the list 71b displays "System abnormality: none". It should be noted that system abnormality may be determined depending on whether the first management value is within its reference range.

Every time the analysis unit 60 obtains a third management value in the quality control mode, the analysis unit 60 may store the obtained third management value in the storage 60a. In this case, by observing the change in the third management value over time, it is possible to predict deterioration of the reagents 41 and 42, and to predict replacing time of the reagents 41 and 42.

Embodiment 2

In Embodiment 2, the configuration of the particle analyzer 10 is the same as that in Embodiment 1, and only the process of staining abnormality determination is different from that in Embodiment 1, as described below.

Figure 11A:
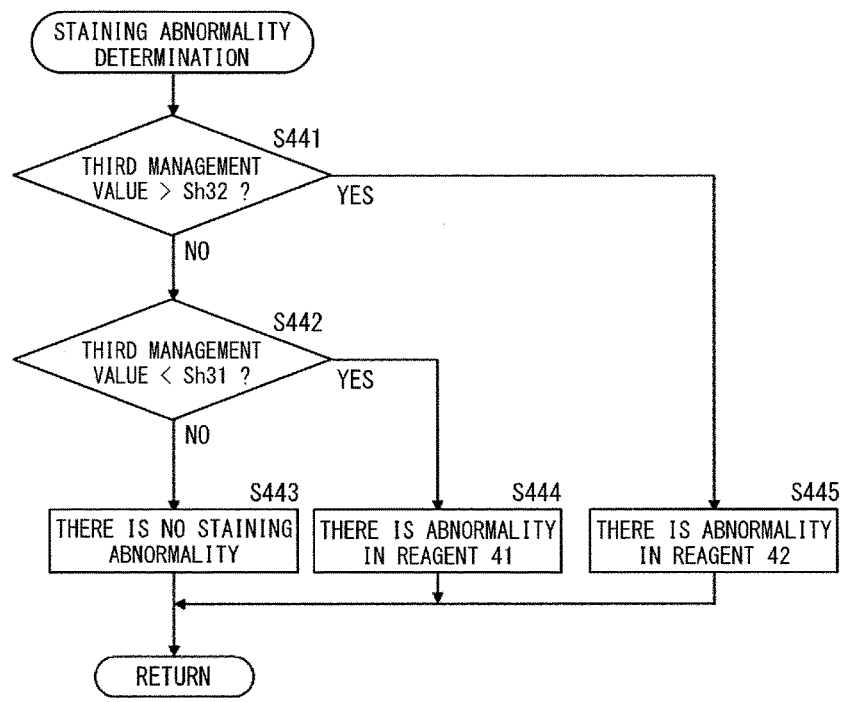
FIG. 11A is a flow chart showing staining abnormality determination according to Embodiment 2.

As shown in FIG. 11A, in step S441, the analysis unit 60 determines whether the third management value is greater than a threshold Sh32. When having determined as NO in step S441, then, in step S442, the analysis unit 60 determines whether the third management value is smaller than a threshold Sh31.

When having determined as NO in step S441 and having determined as NO in step S442, then, in step S443, the analysis unit 60 determines that there is no staining abnormality. When having determined as NO in step S441 and having determined as YES in step S442, then, in step S444, the analysis unit 60 determines that there is abnormality in the reagent 41. When having determined as YES in step S441, then in step S445, the analysis unit 60 determines that there is abnormality in the reagent 42. The analysis unit 60 may perform the determination in steps S441 and S442 by use of the coordinate space shown in FIG. 8B.

Figure 11B:
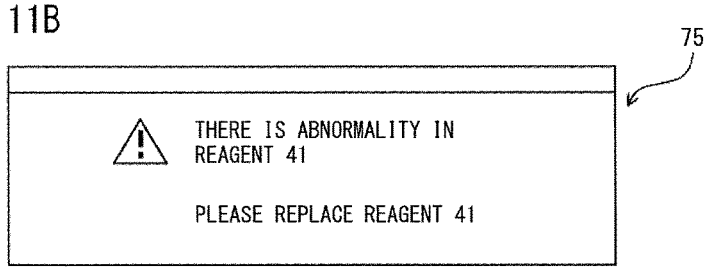
FIG. 11B shows a screen to be displayed on the output unit according to Embodiment 2.
Figure 11C:
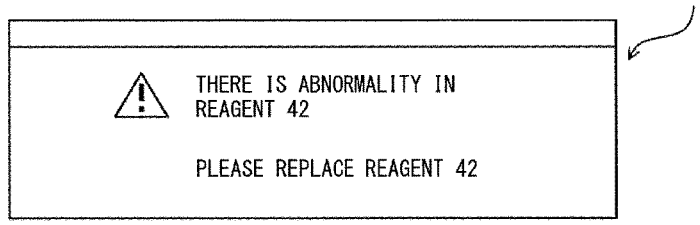
FIG. 11C shows a screen to be displayed on the output unit according to Embodiment 2.

When it has been determined that there is abnormality in a reagent in step S444, S445, a message urging replacement of the reagent is displayed in a later stage of step S212, S215 in FIG. 4. Specifically, when having determined that there is abnormality in the reagent 41 in step S444, the analysis unit 60 displays a screen 75 shown in FIG. 11B on the output unit 70. When having determined that there is abnormality in the reagent 42 in step S445, the analysis unit 60 displays a screen 76 shown in FIG. 11C on the output unit 70.

Here, the case where it is determined that there is staining abnormality in the process of the staining abnormality determination in Embodiment 1 shown in FIG. 7B includes a case where the reagent 41 containing the fluorescent dye has been deteriorated and a case where the reagent 42 containing the RNA remover has been deteriorated. In the case where the reagent 41 has been deteriorated, staining of the first control particles 12a becomes insufficient, and thus, fluorescence generated from the first control particles 12a become weak, causing a decreased third management value. In the case where the reagent 42 has been deteriorated, removal of free RNA becomes insufficient, and thus, background of fluorescence is increased, causing an increased third management value. Therefore, by comparing the third management value with the lower limit threshold Sh31, it is possible to determine that there is abnormality in the reagent 41. By comparing the third management value with the upper limit threshold Sh32, it is possible to determine that there is abnormality in the reagent 42.

Thus, according to Embodiment 2, as in Embodiment 1, it is possible to determine that there is staining abnormality, and further, it is possible to know which of the reagents 41 and 42 should be replaced.

<Experiment Regarding Abnormality Determination>

Next, an experiment actually conducted regarding abnormality determination will be described.

1. Material

The first control particles 12a, the second control particles 12b, the reagent 41, and the reagent 42 used in the experiment were as follows.

The first control particles 12a were prepared as follows. [C33A Cells (HTB-31)] available from American Type Culture Collection were suspended in [PreservCyt®] available from Hologic Inc. and left still for 24 hours. Then, the mixture was centrifuged to remove the supernatant. The resultant mixture was suspended in pH7.5, 10 mM Tris hydrochloric acid aqueous solution. This final mixture was used as the first control particles 12a. As the second control particles 12b, [AlignFlow Plus Flow Cytometry Alignment Beads (A-7303)] available from Life Technologies Inc. diluted by pH7.5, 10 mM Tris hydrochloric acid aqueous solution were used.

As the reagent 41, [Propidium Iodide (PI)] available from Sigma-Aldrich Co. LLC. diluted by ethylene glycol was used. The reagent 41 was prepared in two types. That is, after the reagents 41 were prepared, one was stored with light blocked and the other was stored under exposure to light. Thus, the reagent 41 stored with light blocked, and the reagent 41 stored under exposure to light to be deteriorated were used as the reagent 41. As the reagent 42, [RNaseA (Cat. R4642)] available from Sigma-Aldrich Co. LLC. diluted by pH7.5, 10 mM Tris hydrochloric acid aqueous solution was used.

2. Condition

In the experiment, in order to reproduce abnormality in the reagent 41 being a stain liquid and sensitivity abnormality in the optical detection unit 50, the reagent 41 and the voltage applied to the optical detector 56 which detects fluorescence were changed in accordance with the following three conditions.

Condition 1: the reagent 41 was the one stored under exposure to light; and the voltage applied to the optical detector 56 was 251 V, which was an appropriate voltage.

Condition 2: the reagent 41 was the one stored under exposure to light; and the voltage applied to the optical detector 56 was 255 V.

Condition 3: the reagent 41 was the one stored with light blocked; and the voltage applied to the optical detector 56 was 253 V.

3. Experiment Procedure

In the experiment, measurement regarding the first control particles 12a and measurement regarding the second control particles 12b were separately performed. That is, in the flow chart shown in FIG. 4, steps S202 to S205 were replaced with step S221 to S228 in FIG. 6. The following explanation will be given with reference to the flow charts in FIG. 4 and FIG. 6 as appropriate.

In step S221 in FIG. 6, the reagent 42 and a diluent were added to the first control particles 12a, and the mixture was left still at 37° C. for 10 minutes. Then, the reagent 41 was added thereto, and the resultant mixture was left still at 37° C. for 2 minutes. In this manner, a mixture of the first control particles 12a was prepared. In step S222 in FIG. 6, by use of the particle analyzer 10 shown in FIG. 1, fluorescence signals from the mixture were obtained. Steps S221 to S223 were repeated twice, to obtain a first measurement value of the first round, and a first measurement value of the second round.

Next, in step S225 of FIG. 6, a diluent was added to the second control particles 12b, to prepare the second control particles 12b. In step S226 in FIG. 6, by use of the particle analyzer 10 as in step S222, fluorescence signals from the second control particles 12b were obtained. Steps S225 to S227 were repeated twice, to obtain a second measurement value of the first round and a second measurement value of the second round.

The first measurement values and the second measurement values obtained under Conditions 1 to 3 are shown in the upper tables in FIGS. 12A to 12C. It should be noted that, in FIGS. 12A to 12C, the value of the ratio of each first measurement value to its corresponding second measurement value is shown as a reference.

Next, in step S206 in FIG. 4, as described above, first to third management values were obtained. That is, the first to third management values were obtained with n set at 2 in Expressions (11) to (13). The first to third management values under Conditions 1 to 3 are shown in the lower tables in FIGS. 12A to 12C.

The upper limit thresholds and the lower limit thresholds used in determination on the first to third management values were set as shown in FIG. 12D. Each lower limit threshold was a target value from which a value corresponding to its tolerance was subtracted, and each upper limit threshold was a target value to which a value corresponding to its tolerance was added.

Next, system abnormality determination, detection abnormality determination, and staining abnormality determination were performed. The detection abnormality determination and the staining abnormality determination were performed in accordance with the processes shown in FIGS. 7A and 7B. In order to compare with the technique of U.S. Patent Application Publication No. 2007/013906, system abnormality was determined by use of the same technique as that of U.S. Patent Application Publication No. 2007/013906. That is, when the first management value was greater than or equal to its lower limit threshold, and was smaller than or equal to its upper limit threshold, it was determined that there was no system abnormality. When the first management value was smaller than its lower limit threshold, or was greater than its upper limit threshold, it was determined that there was system abnormality. Determination results of the first to third management values under Conditions 1 to 3 are shown in the lower tables in FIGS. 12A to 12C. In the lower tables in FIGS. 12A to 12C, in the case where a management value is greater than or equal to its lower limit threshold, and is smaller than or equal to its upper limit threshold, determination becomes "G". When a management value is smaller than its lower limit threshold, or is greater than its upper limit threshold, determination becomes "NG".

4. Experiment Result

As shown in the lower tables in FIGS. 12A to 12C, in the case of using the reagent 41 which was intentionally deteriorated by being stored under exposure to light, that is, in the case of Conditions 1 and 2, the third management value was smaller than its lower limit threshold, and the determination on the third management value was "NG". In the case where the sensitivity of the optical detector 56 was intentionally increased, that is in the case of Conditions 2 and 3, the second management value was greater than its upper limit threshold, and the determination on the second management value was "NG".

The experiment above has revealed that, under Condition 1 using the reagent 41 stored under exposure to light, even though the determinations on the first management value and the second management value were both "G", i.e., there was no abnormality in the system and the detection, the determination on the third management value was "NG", i.e., there was abnormality in staining. This abnormality is the one that cannot be found by the technique of U.S. Patent Application Publication No. 2007/013906 which focuses only on the amount of fluorescence of the first control particles 12$a$ (first management value) and the amount of fluorescence of the second control particles 12$b$ (second management value).

In this point, according to the techniques in Embodiments 1 and 2, the third management value representing the staining state is obtained separately from the first management value, whereby it is possible to find abnormality in the staining step which was not grasped conventionally. By replacing the relevant reagent to cause the third management value to be within the reference range, the operator can perform maintenance such that appropriate DNA amount analysis can be performed.

In Conditions 2 and 3, the determinations on the first management value were the same with each other, and the determinations on the second management value were the same with each other. However, under Condition 2 using the reagent 41 stored under exposure to light, the determination on the third management value was "NG", i.e., that there was abnormality in staining was shown. Under Condition 3 using the reagent 41 stored with light blocked, the determination on the third management value was "G", i.e., that there was no abnormality in staining was shown. The difference in the determination between Condition 2 and Condition 3 cannot be found either, by the technique of U.S. Patent Application Publication No. 2007/013906 which focuses only on the amount of fluorescence of the first control particles 12$a$ (first management value) and the amount of fluorescence of the second control particles 12$b$ (second management value).

The technique of U.S. Patent Application Publication No. 2007/013906 does not provide indices for determining a case where the second management value indicates abnormality, i.e., a case there is abnormality in the optical detection unit, and further, for determining whether there is abnormality also in the staining step. In the case where there is abnormality in both of the optical detection unit and the staining step, the operator performs reagent replacement in addition to sensitivity adjustment of the optical detection unit. However, with the conventional technique, whether the abnormality requires reagent replacement is unknown.

In this point, according to the techniques of Embodiments 1 and 2, based on the third management value which is the value of the ratio of the first management value to the second management value, detection abnormality and staining abnormality can be separately determined. Therefore, it is seen that staining abnormality that cannot be determined from the first management value and the second management value can be determined by use of the third management value. Thus, it is seen that, according to Embodiments 1 and 2, even in the case where there is abnormality in both of the optical detection unit 50 and the specimen preparation unit 40, it is possible to individually and assuredly make notifications of the detection abnormality and the reagent abnormality.

What is claimed is:

1. A method performed by a particle analyzer for determining an abnormality in a particle analysis process carried out by the particle analyzer, the method comprising:
    mixing first control particles and fluorescence emitting second control particles with a fluorescent stain in a specimen preparation unit,
    wherein the first control particles react with the fluorescent stain and the second control particles do not react with the fluorescent stain;

irradiating the first control particles and the second control particles flowing in a flow cell with light, and detecting fluorescence from the first control particles and the second control particles;

obtaining a first management value indicating a detection result of the fluorescence emitted from the first control particles and a second management value indicating a detection result of the fluorescence emitted from the second control particles, wherein the first management value is based on an intensity of detected fluorescence from the first control particles, and the detection result is related to an abnormality in the specimen preparation unit or detecting fluorescence from the first control particles, and wherein the second management value is based on an intensity of detected fluorescence from the second control particles, and the detection result is related to an abnormality in detecting fluorescence from the second control particles;

calculating a third management value by dividing the first management value and the second management value, or a ratio of the first management value and the second management value by an analysis unit that determines an abnormality in specimen preparation of the first control particles and the second control particles when the third management value or the ratio of the first and second management values is outside of an upper threshold and a lower threshold; and displaying, on an output unit, a screen showing a message to suggest replacement of the fluorescent stain when an abnormality is determined based on the third management value or the ratio.

2. The method for determining abnormality of claim 1, further comprising determining abnormality in the detecting fluorescence from the first control particles and the second control particles based on the second management value.

3. The method for determining abnormality of claim 1, further comprising prohibiting measurement on a clinical sample by the particle analyzer in a case where the second management value indicates abnormality and in a case where the ratio or the third management value is outside of the upper threshold and lower threshold.

4. The method for determining abnormality of claim 1, further comprising displaying a list including:
an abnormality determination result based on the second management value; and
an abnormality determination result based on one of the ratio or the third management value.

5. The method for determining abnormality of claim 1, wherein the first control particles are selected from the group consisting of cells, polyacrylamide particles, hydrophilic vinyl polymer particles, latex particles, and silica particles.

6. The method for determining abnormality of claim 1, wherein the first control particles are cells, and nuclei of the cells are stained with the fluorescent stain.

7. The method for determining abnormality of claim 6, further comprising contacting the first control particles with RNA remover.

8. The method for determining abnormality of claim 7, wherein,
in a case where the third management value is smaller than the lower threshold, it is determined that there is abnormality in the fluorescent stain, and
in a case where the third management value is greater than the upper threshold, it is determined that there is abnormality in the RNA remover.

9. The method for determining abnormality of claim 1, wherein the particle analyzer analyzes an amount of DNA of each of cells contained in a sample.

10. The method for determining abnormality of claim 1, wherein the particle analyzer analyzes an amount of DNA of each of cells contained in a sample to calculate a number of cells containing a predetermined amount or more of DNA.

11. The method for determining abnormality of claim 1, wherein the first management value is a value based on a representative value of a numerical value obtained from waveforms of fluorescence signals of the respective first control particles, and
the second management value is a value based on a representative value of a numerical value obtained from waveforms of fluorescence signals of the respective second control particles.

12. A method performed by a particle analyzer for determining abnormality in a particle analysis process carried out by the particle analyzer which analyzes, based on a signal waveform of fluorescence emitted from a fluorescence-stained cell nucleus, an amount of DNA contained in the cell nucleus, the method comprising:
mixing first control particles and fluorescence emitting second control particles with a fluorescent stain in a specimen preparation unit,
wherein the first control particles react with the fluorescent stain and the second control particles do not react with the fluorescent stain;
irradiating with light the first control particles and the second control particles flowing in a flow cell, and obtaining signal waveforms based on fluorescence from each first control particle and each second control particle;
obtaining a representative value of an area of a signal waveform of the fluorescence from each first control particle as a first fluorescence area, wherein the first fluorescence area is based on an intensity of detected fluorescence from the first control particles and is related to an abnormality in the specimen preparation unit or detecting fluorescence from the first control particles;
obtaining a representative value of an area of the signal waveform of the fluorescence from each second control particle as a second fluorescence area, wherein the second fluorescence area is based on an intensity of detected fluorescence from the second control particles and is related to an abnormality in detecting fluorescence from the second control particles;
calculating a ratio of the first and second fluorescence areas by an analysis unit that determines an abnormality in staining performed in the particle analyzer when the ratio is outside of an upper threshold and a lower threshold; and
displaying, on an output unit, a screen showing a message to suggest replacement of the fluorescent stain when an abnormality is determined based on the ratio.

13. The method for determining abnormality of claim 12, wherein the first control particles are cells.

* * * * *